United States Patent [19]

Dahlin

[11] Patent Number: 4,803,867
[45] Date of Patent: Feb. 14, 1989

[54] FLUID MEASUREMENT APPARATUS PROVIDING FLOW TUBE STRAIN RELIEF

[76] Inventor: Erik B. Dahlin, 1936 Arroyo Seco Dr., San Jose, Calif. 95125

[21] Appl. No.: 43,341

[22] Filed: Apr. 28, 1987

[51] Int. Cl.$^4$ ............................ G01N 9/00; G01F 1/84
[52] U.S. Cl. .................................. 73/32 A; 73/861.38
[58] Field of Search .............. 73/32 A, 861.37, 861.38

[56] References Cited

U.S. PATENT DOCUMENTS

| | | |
|---|---|---|
| 3,298,221 | 1/1967 | Miller et al. |
| 3,329,019 | 7/1967 | Sipin . |
| 3,355,944 | 12/1967 | Sipin . |
| 3,485,098 | 12/1969 | Sipin . |
| 3,983,744 | 10/1976 | Agar ................................. 73/32 A |
| 4,109,524 | 8/1978 | Smith . |
| 4,354,377 | 10/1982 | Stansfield ........................ 73/32 A |
| 4,559,833 | 12/1985 | Sipin ................................ 73/861.38 |
| 4,622,858 | 11/1986 | Mizerak ........................... 73/861.38 |

FOREIGN PATENT DOCUMENTS 1432165  4/1976  United Kingdom .

OTHER PUBLICATIONS

Solartron Transducer Group Brochure, (8 pages including cover).

*Primary Examiner*—John Chapman
*Attorney, Agent, or Firm*—Ciotti & Murashige, Irell & Manella

[57] ABSTRACT

A fluid meter, such as a density meter or a Coriolis-type mass flow meter is disclosed in which the fluid tube is mounted to allow for expansion and contraction relative to a base to which opposite ends of the tube are mounted. In the preferred embodiments, a single, rectilinear flow tube measuring section is bounded at each end by a thermally insulating wall having a linear bearing which allows longitudinal axial movement while restraining transverse movement. Disposed distally of the linear bearing relative to the flow tube measuring section is means for accommodating the expansion and contraction of the measuring section. In one embodiment this is in the form of a laterally coiled tube portion. In a serial double-tube flow sensor, three serial rectilinear and parallel sections of the flow tube pass through linear bearings similar to that of the single tube, with arcuate sections joining adjacent rectilinear sections. In a third embodiment, the flow is split into two parallel tubes, one end is mounted to the base or housing by a compressible section and the other end is fixedly mounted directly to the base. The two parallel rectilinear measuring sections pass through linear bearings subsequent to the inlet flow splitter and prior to the outlet flow combiner.

19 Claims, 3 Drawing Sheets

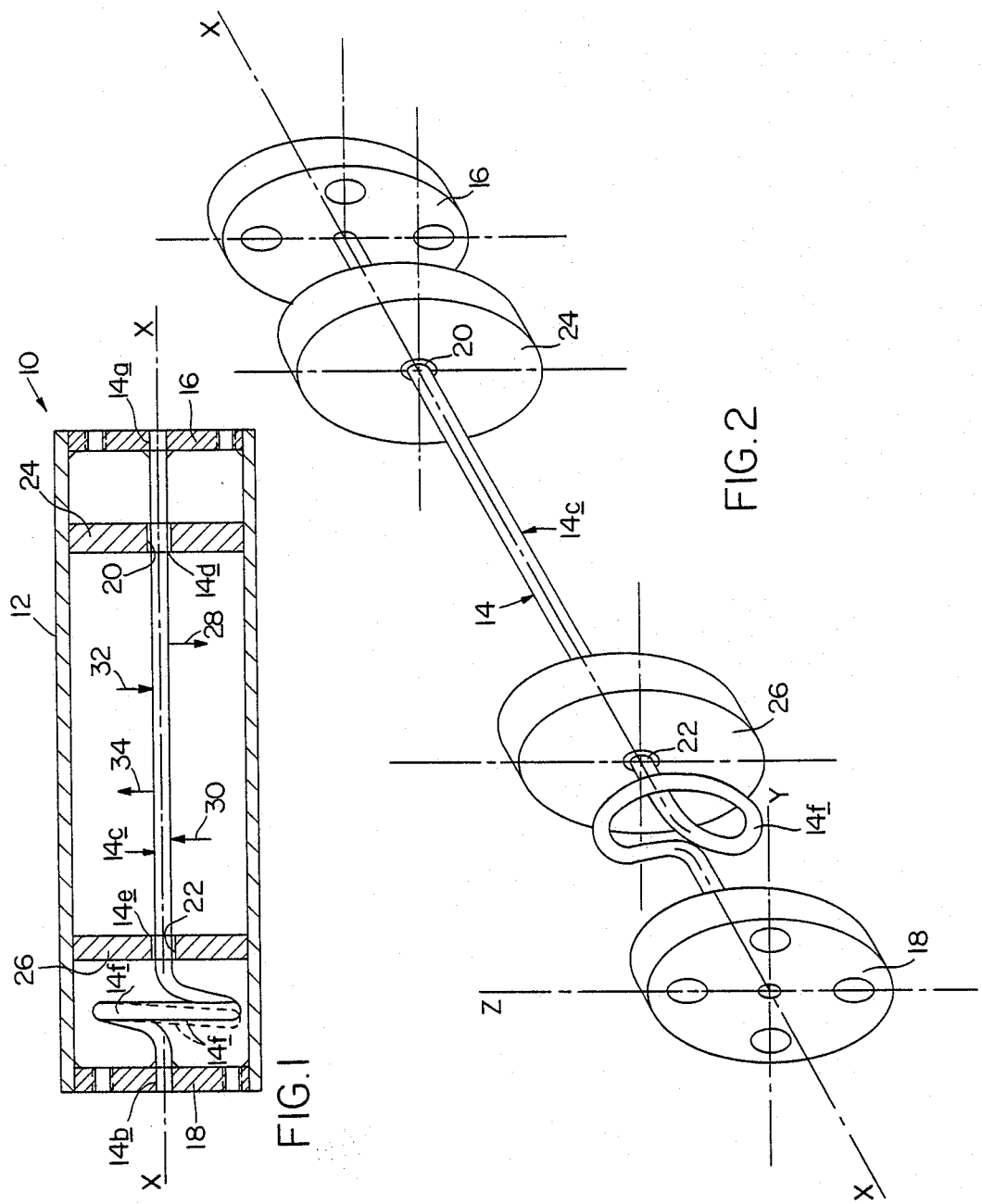

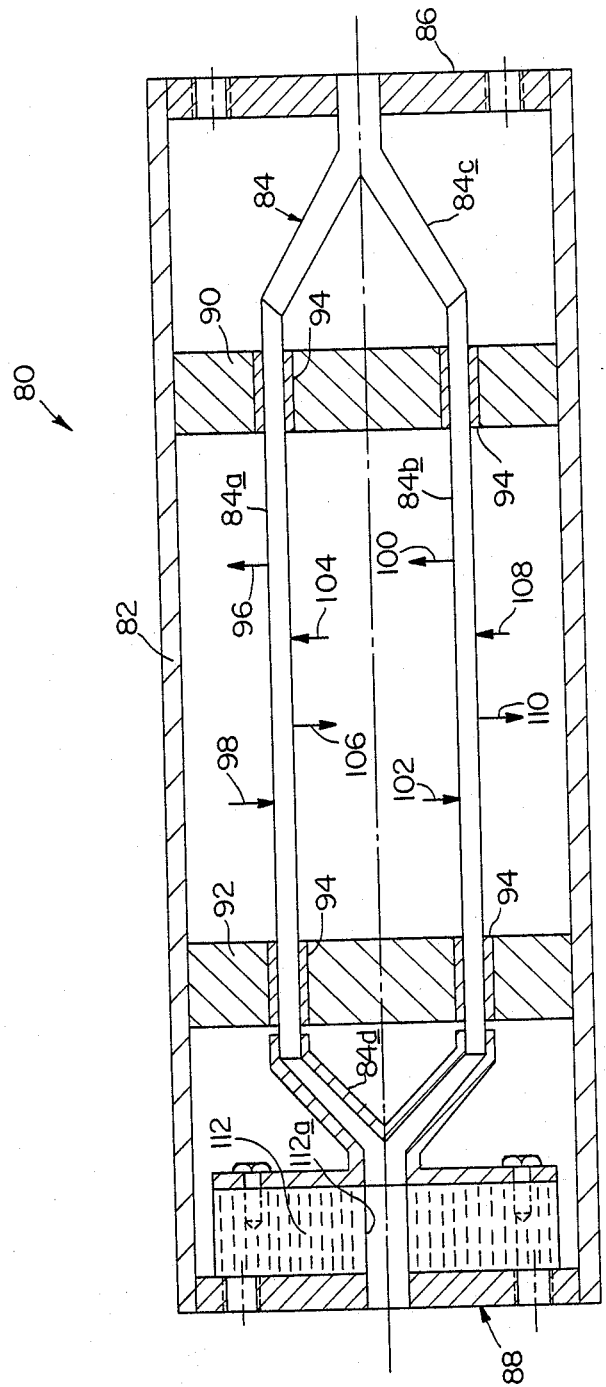

FLUID MEASUREMENT APPARATUS PROVIDING FLOW TUBE STRAIN RELIEF

BACKGROUND OF THE INVENTION

This invention is in the field of measurement of properties of a fluid in a pipe. More particularly, it concerns fluid meters which employ one or more vibrating tubes containing a measurement fluid and which accommodate displacement of the measurement tubes relative to the mounting structure due to changes in fluid or environment temperature or changes in the forces which attach the device to external pipes or other equipment.

BACKGROUND

This invention is applicable to direct mass flow meters based on the Coriolis force principle and to certain densitometers (density meters). Both types employ one or more vibrating tubes through which the fluid to be measured is passed. Hence, as used in the application, fluid meters refer specifically to those fluid meters employing at least one vibrating tube.

Mass flow meters (or direct mass flow meters) have sensing means which respond uniquely to mass flow rate. Other flow meters employ, for example, sensing means which respond to differential pressure or fluid velocity. If one needs to measure mass flow rate with such devices, one must perform separate measurement of density and infer some flow distribution pattern in the cross section of the meter and also infer fluid flow pattern, such as turbulence. They also require Newtonian fluid behavior, which is often not met.

Thus for reason of measurement simplicity alone, direct mass flow meters are very desirable. Additionally, other flow meters generally lend themselves much better to volume flow rate measurement (gallons/minute or liter/second) than to mass flow measurement (tons/hour or kilograms/second). In practice the mass flow measurement is much more useful because chemical reactions require blending of proportional mass (and not volume) of ingredients and product specifications mostly refer to mass percentage of ingredients not volume percentage. Thus, this represents another major advantage of direct mass flow measurement over other techniques.

An example of a direct mass flow meter is a Coriolis flow meter. These meters employ the principle of the Coriolis force and use the influence of a pattern of such forces upon a flow tube carrying the fluid within the meter. Devices disclosed to data employ one or two flow tubes which may split the fluid stream and carry a fraction each or may carry the fluid stream serially through both tubes. The flow tubes are typically vibrated through magnetic force coupling between a drive coil and permanent magnet, one or both of which are attached to a flow tube. To permit attachment to an outside pipe the end of the flow tubes do not participate in the vibration.

For each part of a flow tube which is momentarily not parallel with the axis of rotation of the element, a Coriolis force is produced. The force acts through the body of the fluid to produce pressure on the flow tube wall. The magnitude of the Coriolis force is proportional to the mass flow rate, the angular velocity of rotation and the sine of the angle between flow direction within the element and the direction of the rotation vector.

Under the aggregate of Coriolis forces upon the different parts of the flow tube, the flow tube will have motion in addition to the motion caused by the drive (vibrating) motion. "Motion" in this application is used to describe position, velocity, acceleration of a point or aggregate of points on the flow tube or any time-derivative or time-integral of these variables. Over the time of a single flow measurement, the flow tubes' motion is periodic in any one of these physical variables for almost any point on the flow tube. This together with known vibrating frequency and amplitude permits determination of the flow rate. The dependency of flow rate determination on drive frequency and amplitude has been of fundamental importance in the design of prior Coriolis mass flow meters.

There is little distinction in principle between Coriolis flow meters of one or two tube design especially when in a two tube design the tubes are symmetrical and the measurement reference for drive and motion sensing of one flow tube is the other flow tube. A single flow tube device must use a reference which is not a tube with process fluid. It can be a tube without process fluid, a blade spring or the reference can be the housing itself. A major consideration is mounting requirements to eliminate influence from floor vibrations or pressure pulsation in the process fluid. Another major consideration is that the calibration of the flow meter does not degenerate excessively when the fluid density changes.

When mass flow rate changes the motion changes which is the principle of the flow measurement. However, if the drive amplitude changes, the Coriolis portion of the motion changes also. If one did not know the new amplitude (for example, by absence or inaccuracy of amplitude measurement), the flow meter may not distinguish a flow rate change from the amplitude change. Fluid pressure change modifies the cross sectional dimension of the flow tube end, and thereby, its bending properties. Large pressure changes which may occur in practice can jeopardize calibration accuracy unless the flow meter design eliminates this hazard.

These considerations are dealt with in many of the existing known devices. In particular, reference is made to my copending U.S. patent application Ser. No. 873,201, filed June 11, 1986 and entitled "Coriolis-Type Mass Flowmeter."

Such conventional flow meters mount the opposite ends of the flow meter measurement tube rigidly to a base or housing and vibrate the tube section extending therebetween. If the flow tube, especially a straight or near straight flow tube, is exposed to longitudinal axial forces at the mounting location, the vibrating frequency (drive frequency) will change. The situation is similar to a violin string which has a higher natural frequency if pulled tighter. The axial forces may be caused by mounting forces such as pull by the screws attaching the sensor to surrounding pipes or they may be caused by the flow tube undergoing a thermal expansion or contraction different from simultaneous thermal expansion or contraction of the housing. Thus, if the housing and the flow tube have the same length change, no axial forces are produced. It is possible to compensate for a difference in dimension change by measuring the differential temperature change of the flow tube and housing. From a predetermined calibration, the flow reading based on the magnitude of the differential temperature may be corrected. However, this still makes the sensor vulnerable to axial forces caused by mounting to surrounding pipes.

Density meters are used to determine the density of a fluid in a conduit (pipe). They are useful for determination of product quality, composition and for mass flow measurement when combined with a volumetric flow meter. In the latter application, mass flow rate is computed as the product of density and volumetric flow rate.

The type of density meters pertaining to this invention employ a vibrating tube or a combination of two or more such tubes. The fluid to be measured passes through the vibrating tube(s). The frequency of vibration is one of the natural frequencies of the tube, for example, the first, second or third mode. A drive system typically consisting of a coil and a magnet sustain the vibration at the natural frequency or immediate vicinity thereof. The natural frequencies are dependent upon the mass per unit area of tube and fluid in the tube. For example, for a straight uniform tube:

$$\text{Natural frequency} = \text{constant} * ((EI)/(QL^4))^{\frac{1}{2}}$$

where
E = elasticity modulus;
I = moment of inertia for tube cross-section;
Q = mass per unit length of tube and fluid; and
L = tube length.

The fluid density will influence Q which consists of two components, one derived from the tube itself and the other from the fluid as follows:

$$Q = Q_{tube} + A * \text{Density},$$

where
A = fluid cross-section.

By measurement of the natural frequency of vibration the density can be computed from these two formulas or other similar formulas for tubes which are not straight and uniform.

The measurement of the natural frequency is well known. One can for example use a magnet and coil sensor with one of these elements attached to the tube and the other fixed. At zero crossing of the signal from the coil a counter is started. At the next zero crossing the counter is stopped. The natural frequency is then determined by $$\text{Natural frequency (Hz)} = F/C,$$

where
F = oscillator frequency used by the counter (Hz); and
C = count between zero crossings.

The sensing device for the frequency may be located at a point on the flow tube such as at a node for a particular mode other than the drive mode which is different from the location of the drive coil/magnet. It is also possible to evaluate the frequency using no separate sensor for the frequency at all and instead determine the frequency from the signals existing in the drive control loop itself.

Axial forces caused by thermal expansion or contraction of the tubes in relationship to the housing or by axial mounting forces will also influence the natural frequency as was explained previously for the Coriolis flow meters. Note, however, that this phenomenon is not included in the first formula given above.

Axial forces can be produced thermally by change of fluid temperature in the flow tube. Such a change produces three different effects of concern to the sensor:

1. steady state differential thermal dimension change between flow tube and housing thereby producing axial forces as discussed;
2. transient differential change of the dimension between flow tube and housing due to gradual heat transfer from fluid to the housing or vice versa (this leads to a slow shift in calibration after fluid temperature change or change of the ambient temperature around the housing); and
3. change of elasticity coefficient for the flow tube due to change of Young's modulus (elasticity modulus) with temperature.

For a straight stainless steel flow tube, the effect upon drive frequency and calibration caused by the first effect is typically four to six times larger than the effect of the third effect assuming that the flow tube is rigidly mounted at both ends. In the prior art the effect of the change of the elasticity coefficient for the flow tube has been compensated but no disclosure is known for compensation of the first and second effects which for a straight flow sensor are more important. Some devices which inherently relieve longitudinal stress are disclosed by Sipin in U.S. Pat. Nos. 3,355,944; 3,485,098; and 3,329,019, all entitled "Mass Flowmetering Means"; by Smith in U.S. Pat. No. 4,109,524, entitled "Method and Apparatus for Mass Flow Rate Measurement"; by Miller et al. in U.S. Pat. No. 3,298,221, entitled "Densitometer"; and by Catherall in British Pat. No. 1,432,165, entitled "Improvements in Apparatus for Determining the Density of a Fluid". Similar devices are known to be made commercially by Solartron of Farnborough, Hants., U.K.

In particular, FIG. 7 of U.S. Pat. No. 3,329,019 discloses a straight flow tube which is connected at opposite ends to baffles which are connected to portions of the flow tube connected to the housing. These baffles are intended to provide lateral displacement during the vibrating of the measuring portion of the flow tube. Even with the baffles used as indicated, it has been found that they are very sensitive to changes in the temperature and other dynamic factors effecting operation of a Coriolis flow meter. The baffles themselves actually become part of the vibrating structure and influence the effectiveness of the metering device.

This is similar to the function of the baffles disclosed in U.S. Pat. No. 4,109,524 in which a center tube section is connected with bellows to the outer sections. A mechanical drive in the center moves the side sections.

SUMMARY

The present invention provides a mass flow meter which overcomes the noted disadvantages of the prior art with regard to their inability to accommodate longitudinal axial stress changes resulting from thermal expansion and contraction or tube mounting. More particularly, the present invention provides a flow meter wherein the section to be vibrated is isolated in a manner allowing axial changes in the flow meter tube while controlling the transverse movement of the tube at the end portions of a measuring section.

In a preferred embodiment of the invention, opposite ends of a flow tube of a mass flow meter are rigidly mounted to a base or housing. A measuring tube section forming a portion of the mass flow tube is constrained on at least one end by a linear bearing which allows longitudinal axial movement therethrough while restraining lateral forces. This section of the mass flow tube is vibrated for measuring the mass traveling in the tube. Interposed the linear bearing and the corresponding fixed end of the flow tube is means for accommodating longitudinal axial displacement of the tube. Further, the measuring section is preferably fixed to the base by thermally insulating walls which minimize the amount of heat flow between the tube and the housing. This provides for achieving very quickly a steady state temperature condition in the flow tube, thereby expediting the recalibration of the meter as a result of a temperature change.

It can be seen that the present invention provides a flow meter having a measuring flow tube section which is minimally effected by changes in the flow tube dimensions resulting from temperature changes, thereby minimizing the effect of the temperature changes on the operative characteristics of the flow tube meter. These and other features and advantages of the present invention will be more clearly understood from a consideration of the drawings and the following detailed description of the preferred embodiments.

BRIEF DESCRIPTION OF THE DRAWINGS

The drawings are not to scale and some dimensions are distorted for the purpose of illustration. Like elements are referred to by like numerals in the drawings.

FIG. 1 is an elevational, sectional view of a first preferred embodiment Coriolis flow meter of the invention.

FIG. 2 is a perspective view of the flow tube and mounting members of the flow meter of FIG. 1.

FIG. 5 is a cross-sectional view of yet a third preferred embodiment of the present invention.

DETAILED DESCRIPTION OF THE PREFERRED EMBODIMENTS

Figure 3:
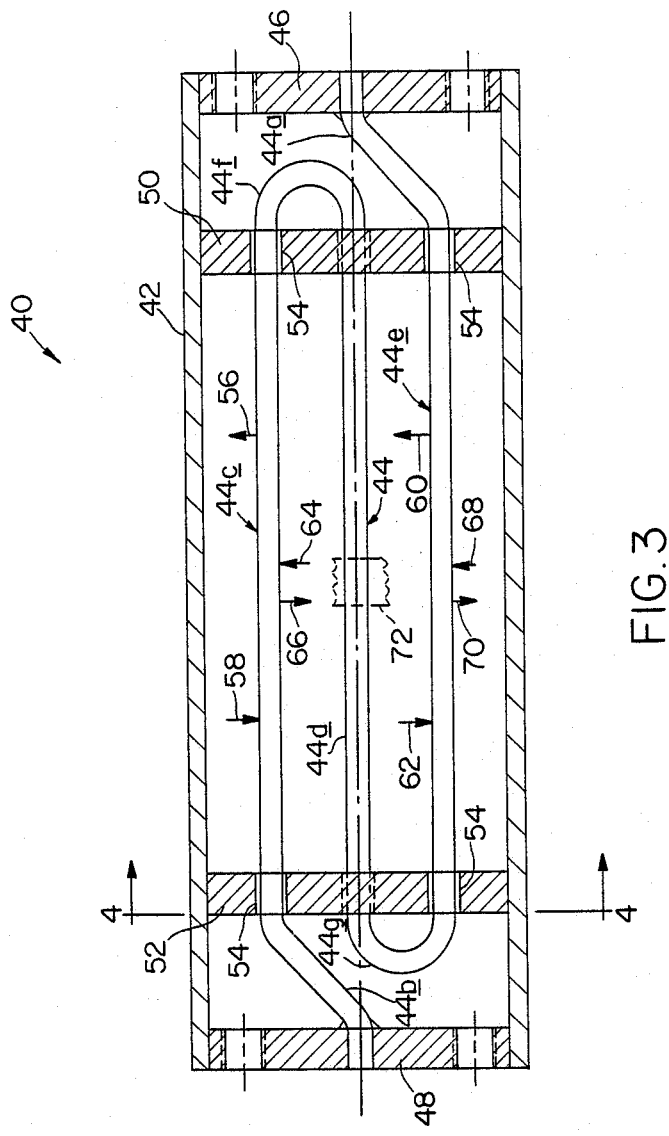
FIG. 3 is a cross-sectional view of a second preferred embodiment of the invention.

The first preferred embodiment of the invention is shown as a Coriolis flow meter 10 in FIGS. 1 and 2. Mass flow meter 10 includes a base or housing 12 relative to which is mounted a flow tube 14. Flow tube 14 is rigidly mounted to housing 12 at opposite ends 14a, 14b, by flanges 16, 18, respectively, to which it is joined by appropriate means, such as welding.

Tube 14 includes an intermediate rectilinear section 14c which will be referred to generally as a measuring or vibrating section. Section 14c extends between opposite ends 14d and 14e, which are disposed in appropriate sliding or linear bearings 20, 22, respectively. These bearings are fixedly mounted on disk-shaped walls 24, 26, respectively. As a salient feature of the present invention, these walls are made of a suitable thermally insulating material, such as plastic or ceramic. Disks 24 and 26 are rigidly mounted around their peripheral edges to housing 12 by appropriate mounting means, such as by adhesive or by mechanical fastening such as by screws (not shown). It will be appreciated that tube 14 could be fixed to disks 24 and 26 with sliding bearings existing between the disks and housing 12. Flanges 16 and 18 are preferably made of a hard rigid material, such as a metal and are appropriately rigidly attached to housing 12 by welding or a screw mounting, and have a plurality of bores for connection to a main pipe.

Flow tube 14 is formed in an arcuate loop or coil 14f interposed flange 18 and disk 26, as shown. Although not shown in these figures, a similar loop can also be introduced between disk 24 and flange 16. This would be a preferable design if it were not for the additional manufacturing expense involved in producing the loop.

As mentioned previously, when the fluid flowing in tube 14 changes temperature, flow tube 14 will change its size, particularly along the direction of the fluid flow. When the fluid increases in temperature, the tube will expand. Conversely, when the temperature decreases, the tube will contract. Such displacements in tube dimension also result from other temperature changes, such as the change in the temperature of housing 12 relative to the material flowing in the tube, such as would result from a change in ambient temperature around meter 10.

When the flow tube expands or contracts due to differential temperature shift between the flow tube and the housing, sliding bearings 20 and 22 permit the resulting forces to be absorbed by the loop which will be slightly moved but not able to produce a strong spring force along the flow tube in the axial direction. This is illustrated by the portion of loop 14f shown in dashed lines (not to scale) which would result from a lengthening of section 14c. Loop 14f thus forms a spring which is very soft by comparison with the spring force produced by axial compression or expansion of a flow tube in the longitudinal axial direction with fixed mountings instead of linear bearings. The loop thus eliminates the problem caused by axial mounting forces and the thermal steady state differential thermal dimension change between the flow tube and housing previously mentioned.

The use of thermally insulating disks 24, 26 compensates for the transient thermal problem due to the gradual heat transfer between the fluid and the housing, described previously. After a fluid temperature change, the flow tube will nearly instantly assume a temperature of that of the fluid uniformly over the whole vibrating domain between the disks 24, 26 and especially including the tube at bearings 20, 22 where the largest bending moment exists. While the temperature shift gives some change of drive frequency, this change is constant and can easily be compensated for by a temperature measurement of the flow tube wall such as is known in the prior art and is not described herein.

Had the disks 24, 26 holding the flow tube been made of a good thermal conducting material the disks and the endpoints of the vibrating section defined by bearings 20, 22 would be exposed to a long term gradual change of temperature when heat is transferred between the flow tube and housing. For a time period typically of as long as ten to twenty minutes, the calibration would shift without the possibility of making a compensation from a flow tube temperature measurement. The flow tubes in prior art designs are mounted with thermally well conducting walls and therefore present this calibration problem.

It will be understood that the present invention could also be provided in an embodiment similar to the embodiment shown in FIGS. 1 and 2 by deleting disk 24 and bearing 20. This would mean that the measuring or vibrating section 14c would be longer. However, thermal expansion or contraction of the flow tube in this section would be accommodated in the spring produced by coil 14f which accommodation would be provided through linear bearing 22.

As a Coriolis flow meter, a drive coil/magnet and sense coil/magnet are attached relative to the vibrating section 14c, as is known in the prior art, and as is particularly described in my copending United States patent application discussed previously having Ser. No. 873,201, filed June 11, 1986, which is incorporated herein by reference. In a second mode installation, two drive coil/magnet assemblies would be connected to vibrate the flow tube 14c at points 28, 30 as an example. Correspondingly, for this arrangement, a pair of sense coil/magnet assemblies would be attached near the center at sense points 32, 34.

Figure 4:
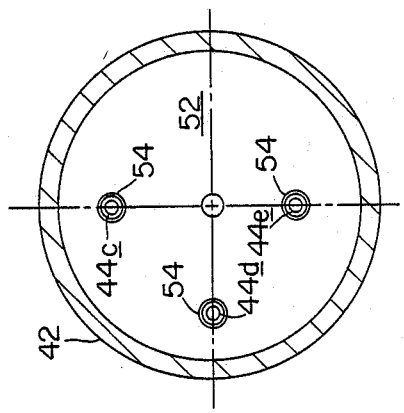
FIG. 4 is a view taken along line 4—4 in FIG. 3.

A second preferred flow meter 40 made according to the present invention is shown in FIGS. 3 and 4. It also includes a housing 42, a flow tube 44, fixed mounting flanges 46, 48, and insulating disks or walls 50, 52. Opposite ends 44a, 44b are respectively fixedly attached to mounting flanges 46, 48, as was the case with the embodiment of FIG. 1. Tube 44 also includes three serial, rectilinear segments 44c, 44d, and 44e, connected as shown. Sections 44c and 44e serve as the measuring or vibrating sections. Sections 44c and 44d are connected by a loop or arcuate section 44f and, similarly, sections 44d and 44e are connected by another arcuate section 44g. These loop sections are disposed externally of insulating disks 50, 52 relative to the corresponding vibrating sections 44c and 44e. All portions of tube 44 passing through insulating disks 50, 52 pass through corresponding linear bearings which are substantially identical and will be given the common reference 54. Tube vibrating sections 44c and 44e are connected, respectively, to drive coil/magnet assemblies at points 56 and 58, and at points 60 and 62 for mode 2 drive. Correspondingly the sensor coil/magnet assemblies are applied at points 64, 66, 68 and 70, as described in my above referenced co-pending application.

When the flanges are exposed to outside axial forces from surrounding pipes or when a temperature differential exists between the housing and the flow tubes, movement of the looped end portions 44f, 44g, in the space between flange 46 and disk 50 and flange 48 and disk 52 will absorb the motion without causing stresses and, thereby, without causing stress-determined frequency and related calibration shift. If the looped end portions are too stiff, a bellows 72, shown in dashed outline could be added into tube section 44d. The thermally insulating disks have the same function in this embodiment as that described with reference to FIGS. 1 and 2.

A third form of preferred embodiment of the present invention is illustrated in the cross-sectional view shown in FIG. 5. A flow sensor 80 includes a housing 82, flow tube 84, mounting flanges 86, 88, insulating walls 90, 92, and linear or sliding bearings 94. Drive coil/magnet assemblies are applied at points 96 and 98 on a first vibrating section 84a and at points 100 and 102 on a second vibrating tube section 84b. The corresponding sensor coil/magnet assembly application points are 104, 106, 108 and 110, as shown.

Tube 84 also includes a flow splitter 84c and a flow combiner 84d. It will be understood that these terminologies could be reversed if the inlet was from the left rather than from the right, as presumed by the terms. Attached to one of the flow splitter or combiner is a compressible tube mounting 112 which effectively forms what may be referred to generally as a portion of a total flow tube including flow tube 84. Compressible mounting 112 includes an inner bore 112a which forms a continuation of the conduit defined by tube 84. Mounting 112 is appropriately attached to the associated flow combiner 84d by appropriate means, such as bolts or screws as shown. Mounting 112 correspondingly is attached to flange 88 by appropriate adhesive means or by a similar screw or bolt, so long as the bolt connections between the flow splitter and flange are not connected, so as to not alter the function of mounting 112. Mounting 112 could also be a bellows or a portion of tube 84 which has a thinner outer wall to render it relatively flexible, or other equivalent axially flexible component. It will thus be appreciated, similar to the previous two preferred embodiments described, that the expansion or contraction of the vibrating sections 84a and 84b is accommodated by mounting 112. This medium could also be located on the opposite end of tube 84 or could alternatively be placed on both ends.

It will therefore be appreciated that the preferred embodiments as described made according to the present invention provide for the accommodation of longitudinal axial stresses in the flow tube due to thermal considerations occurring between the base or housing and the flow tube or due to external stresses applied to the tube mountings. The vibrating sections are isolated by the use of linear or sliding bearings which accommodate the axial changes in dimensions of the flow tube while maintaining the same length of vibrating section. Further, by the use of a relatively insulating material for the disk or wall supporting the linear bearings, steady state temperature conditions are readily reached which would not otherwise be the case with standard highly thermally conductive materials. Thus, the preferred embodiment provides the combined effects of rapidly reaching steady state condition and accommodating expansion and contraction of the flow tube relative to the base or housing.

While the invention has been described with reference to the foregoing preferred embodiments, it will be understood by those skilled in the art that other changes in form and detail may be made, such as those suggested, without departing from the spirit and scope of the invention as defined in the claims.

I claim:

1. A fluid meter for measuring a characteristic of a material flowing therethrough comprising:

a base;

at least one flow tube having an inlet end and an outlet end, said flow tube ends being fixedly mounted to said base, said material flowing through said tube, said at least one flow tube including at least one section having a longitudinal axis and interposed said inlet end and said outlet end and having an end associated with each of said inlet end and said outlet end, at least one of said section ends being spaced from the associated one of said inlet end and said outlet end;

means for vibrating each of said at least one section intermediate said section ends;

at least one linear bearing mounting each of said at least one section end spaced from said associated flow tube end relative to said base in a manner allowing movement of said section end along the longitudinal axis of said section end and preventing movement transverse to said longitudinal axis of said section end in at least the directions of vibrational movement of said section, with said linear bearing being mounted to said base by a thermally insulating material; and means for measuring at least one parameter of the motion of said flow tube section.

2. A fluid meter according to claim 1, wherein said thermally insulating material is plastic.

3. A fluid meter according to claim 1, wherein said thermally insulating material is a ceramic.

4. A fluid meter according to claim 1 wherein said flow tube further comprises means interposed said means mounting said one section end and said associated one of said inlet and outlet ends for accommodating longitudinal axial movement of said tube section relative to said tube end.

5. A fluid meter according to claim 4 wherein said axial-movement-accommodating means comprises an arcuate section of tube.

6. A fluid meter according to claim 5 wherein said arcuate section is in the form of a loop.

7. A fluid meter according to claim 5 wherein said arcuate section is in the form of a coil.

8. A fluid meter according to claim 4 wherein said axial-movement-accommodating means is a section of tube formed in a material having axially compressible tube walls.

9. A fluid meter according to claim 1, wherein said flow tube includes a plurality of said interposed sections, said interposed sections being mutually parallel and having substantially equal lengths, said vibrating means vibrating each of said interposed sections, and at least one end of each of said sections being mounted by one of said linear bearings.

10. A fluid meter according to claim 9 wherein said flow tube interposed sections are mutually coupled to provide fluid flow in series and include a connecting section joining adjacent interposed sections, said connecting section being coupled to said adjacent interposed sections by a stretch of tube transverse to the longitudinal axis of said interposed sections.

11. A fluid meter according to claim 9 wherein said flow tube interposed sections are mutually coupled to provide fluid flow in parallel.

12. A fluid meter for measuring a characteristic of a materal flowing therethrough comprising:
a base;
at least one flow tube having an inlet end and an outlet end, said flow tube ends being fixedly mounted to said base, said material flowing through said tube, said at least one flow tube including a plurality of sections having longitudinal axes and interposed said inlet end and said outlet end with each said interposed section having an end associated with each of said inlet end and said outlet end, at least one of said section ends being spaced from the associated one of said inlet end and said outlet end;
means for vibrating each of said at least one section intermediate said section ends;
a linear bearing mounting each of said at least one section end spaced from said associated flow tube end relative to said base in a manner allowing movement of said section end along the longitudinal axis of said section end and preventing movement transverse to said longitudinal axis of said section end in at least the directions of vibrational movement of said section; and
means for measuring at least one parameter of the motion of said flow tube section; and
wherein said interposed sections are mutually parallel, are mutually coupled to provide fluid flow in parallel, and have substantially equal lengths, said vibrating means vibrating each of said interposed sections, and at least one end of each of said sections being mounted by one of said linear bearings;
wherein said flow tube further comprises a flow splitter for splitting flow from an inlet portion of said flow tube into said interposed sections and a flow combiner for recombining flow from said interposed sections into an outlet tube portion, said fluid meter further comprising means mounting one of said flow splitter and said flow combiner relative to said base for accommodating longitudinal axial movement of said interposed sections relative to said base.

13. A fluid meter according to claim 12 wherein said accommodating means comprises a tube section formed of a material having axially compressible tube walls.

14. A fluid meter for measuring a characteristic of a material flowing therethrough comprising:
a base;
at least one flow tube having an inlet end and an outlet end, said flow tube ends being fixedly mounted to said base, said at least one flow tube including at least one section having a longitudinal axis and interposed said inlet end and said outlet end and having an end associated with each of said inlet end and said outlet end, said interposed section ends being spaced from the associated one of said inlet end and said outlet end;
means for vibrating said at least one interposed section intermediate said section ends;
linear bearing means for supporting each of said interposed section ends relative to said base for allowing movement of said interposed section ends along the longitudinal axis of said interposed section ends and preventing movement transverse to said longitudinal axis;
means mounting said linear bearing means relative to said base for thermally insulating said interposed section tube ends from said base;
means for measuring at least one parameter of the motion of said interposed section; and
means mounting one of said interposed section ends and said associated one of said inlet and outlet ends for accommodating longitudinal axial movement of said interposed section relative to said tube end.

15. A fluid meter according to claim 14 wherein said flow tube includes a plurality of said interposed sections, said interposed sections being mutually parallel and having substantially equal lengths, said vibrating means vibrating each of said interposed sections, and at least one end of each of said sections being mounted by one of said linear bearing means.

16. A fluid meter according to claim 15 wherein said flow tube interposed sections are mutually coupled to provide fluid flow in series and include a connecting section joining adjacent interposed sections, said connecting section being coupled to said adjacent interposed sections by a stretch of tube transverse to the longitudinal axes of said interposed sections.

17. A fluid meter according to claim 15 wherein said flow tube interposed sections are mutually coupled to provide fluid flow in parallel.

18. A fluid meter according to claim 17, wherein said flow tube further comprises a flow splitter for splitting flow from an inlet portion of said flow tube into said interposed sections and a flow combiner for recombining flow from said interposed sections into an outlet tube portion, said fluid meter further comprising means mounting one of said flow splitter and said flow combiner relative to said base for accommodating longitudinal axial movement of said interposed sections relative to said base.

19. A fluid meter according to claim 18 wherein said accommodating means comprises a tube section formed of a material having axially compressible tube walls.

* * * * *